(12) United States Patent
Horowitz et al.

(10) Patent No.: US 6,294,361 B1
(45) Date of Patent: *Sep. 25, 2001

(54) PROCESSES FOR PHOTOREACTIVE INACTIVATION OF A VIRUS IN BLOOD CELL OR COAGULATION FACTOR CONTAINING COMPOSITIONS AND USE THEREOF FOR PREPARING COMPOSITIONS USEFUL FOR TRANSFUSION

(75) Inventors: Bernard Horowitz, New Rochelle; Jay E. Valinsky, New York; Nicholas E. Geacintov, New York; Bolanle Williams, New York; Shanti B. Rywkin, Brooklyn; Henrietta Nunno, New York, all of NY (US)

(73) Assignee: New York Blood Center, Inc., New York, NY (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/958,768

(22) Filed: Oct. 26, 1997

Related U.S. Application Data (63) Continuation of application No. 08/031,787, filed on Mar. 15, 1993, now Pat. No. 6,077,659, which is a continuation of application No. 07/706,919, filed on May 29, 1991, now Pat. No. 5,232,844, which is a continuation-in-part of application No. 07/524,208, filed on May 15, 1990, now Pat. No. 5,120,649.

(51) Int. Cl.[7] ............................. C12N 13/00; C12N 7/04; A01N 1/02
(52) U.S. Cl. .................................. 435/173.3; 435/173.1; 435/236; 435/2
(58) Field of Search ............................. 435/173.1, 173.3, 435/236, 2; 424/90

(56) References Cited

U.S. PATENT DOCUMENTS 4,693,981 * 9/1987 Wiesehahn et al. ................. 435/238

OTHER PUBLICATIONS

Lin et al. (1989), *Blood*, 74(1), 517–525.*
Swartz et al. (1979) *Proc. Soc. Exp. Biol. Med.*, 161, 204–209.*
Bodylak et al. (1983) *J. Clin. Microbiol.*, 17(2), 374–376.*
Sonada et al. (1987) *Photochem. Photobiol.*, 46(5), 625–631.*
Rosenthal et al. (1989) in "Pholocyanines," Lezhoff et al. (EDS), pp. 397–425, VCH Publishers, Inc., New York.*

* cited by examiner

*Primary Examiner*—Jon P. Weber
(74) *Attorney, Agent, or Firm*—Amster, Rothstein & Ebenstein (57) ABSTRACT

The present invention concerns a process for inactivating an extracellular lipid enveloped human pathogenic virus and/or an intracellular human pathogenic virus which may be present in a blood cell composition containing $\geq 1 \times 10^9$ cells/ml by contacting that composition with a virucidally effective amount of at least one photoreactive compound having an absorption maximum of $\geq 630$ nm, light and oxygen and/or a quencher. In one embodiment of the invention, the process is conducted under conditions whereby a structural integrity of greater than 80% of at least one type of blood cell contained within said composition is retained. Another embodiment of the invention relates to a process for inactivating an extracellular lipid enveloped human pathogenic virus and/or an intracellular human pathogenic virus which may be present in a composition containing at least one coagulation factor while retaining at least 77% of said coagulation factor by contacting said composition with a virucidally effective amount of at least one photoreactive compound, light and a quencher. The processes of the invention can be used to prepare blood products, which, in turn, are suitable for transfusion into a recipient in need of such transfusion.

21 Claims, 3 Drawing Sheets

PROCESSES FOR PHOTOREACTIVE INACTIVATION OF A VIRUS IN BLOOD CELL OR COAGULATION FACTOR CONTAINING COMPOSITIONS AND USE THEREOF FOR PREPARING COMPOSITIONS USEFUL FOR TRANSFUSION

This is a continuation of application Ser. No. 08/031,787 filed on Mar. 15, 1993, now U.S. Pat. No. 6,077,659.

Which is a division, of application Ser. No. 07/706,919, filed May 29, 1991, now U.S. Pat. No. 5,232,844, which is a CIP of U.S. Ser. No. 07/524,208 filed May 15, 1990, now U.S. Pat. No. 5,120,649.

GOVERNMENT RIGHTS

This invention was made with United States government support under Grant 1-RO1-HL41221 from the NHLBI. The United States Government has certain rights in this invention.

BACKGROUND OF THE INVENTION

1. Field of the Invention

The present invention concerns a method to inactivate viruses in biological compositions, for example, in whole blood or red blood cell concentrates, without incurring substantial disruption or inactivation of cells, for example, without adversely affecting red blood cell structure or function, by using a photoactive compound, for example, a phthalocyanine, together with light exposure and variations thereon.

2. Description of Related Art

Nature of the Concept

Substantial progress has been made in reducing the viral infectivity of whole blood and its components through improved donor selection and donor blood screening procedures. Despite this progress, there is a continued risk of transmission of viruses including hepatitis viruses and human immunodeficiency viruses (HIV) by whole blood and blood products.

The risk of transmission of certain viruses (e.g., hapatitis B virus (HBV), hepatitis C virus (HCV), human immunodeficiency virus (HIV)) has been considerably reduced and possibly eliminated in coagulation factor concentrates through the application of virucidal procedures during the course of manufacture (Prince, A. M., Horowitz, B., Horowitz, M. S., Zang, E., "The Development of Virus-Free Labile Blood Derivatives—A Review", Eur. J. Epidemiol., 1987; 3:103–118 and Mannucci, P. M., Colombo, M., "Virucidal Treatment of Clotting Factor Concentrates", The Lancet, 1988;782–785). However, when treating coagulation factor concentrates, some viruses (e.g., parvovirus) may remain infectious. In addition, the development of virucidal processes applicable to cell components, i.e., blood cell fractions such as red blood cells or platelets, has been slow, both because cells are more fragile than proteins, and cells serve to harbor and protect virus against inactivation. Nonetheless, if virus transmission by whole blood or blood components is to be eliminated, effective virus removal or potent virucidal methods applicable to blood cells will be required. Since both red blood cells or platelets are non-replicating, approaches directed toward nucleic acid modification might offer the required specificity.

It is important to recognize in assessing virucidal procedures for cell-containing solutions that virus will be present in multiple forms: virus free of the cell; formed virus associated with the cell; functional, but unpackaged viral nucleic acid within the cell; and viral nucleic acid integrated into the cell genome. Each form should be considered infectious and capable of causing viral disease in vivo. Virucidal methods which inactivate virus in one form, e.g., cell-free virus, may not inactivate virus in other forms, e.g., cell-associated forms. Additionally, the presence of cells is known to inhibit the action of both physical and chemical approaches to virus inactivation. Cells compete for added virucidal reagents and absorb radiation which otherwise would be virucidal. Thus, for example, while ultraviolet irradiation is highly virucidal in salt solutions or in dilute protein solution, the degree of virucidal activity is incomplete when treating cell-containing solutions. Furthermore, in this context, it is not sufficient to inactivate virus alone; rather, it is necessary to do so with sufficient vigor that viral infectivity is eliminated without deleterious effects to the valuable cell components, e.g., red blood cells.

Most virucidal procedures which have been developed, e.g., pasteurization or solvent/detergent treatment, cannot be applied to blood cell preparations without damaging the cells and rendering them unfit for transfusion.

Heretofore, it has not been possible to prepare virus sterilized forms of whole blood or red cell concentrates or platelet concentrates where at least $10^4$ infectious units ($ID_{50}$) and preferably $\geq 10^6$ $ID_{50}$ of both intracellular and extracellular virus were inactivated without adversely affecting the cells and/or without using highly toxic agents.

Phthalocyanines

While there has been growing interest in the use of phthalocyanines for the treatment of cancerous cells (Rosenthal, I. and Ben Hur, E., "Phthalocyanines in Photobiology", Lezhoff C. C. and Lever A. B. P. eds., Phthalocyanines, VCH Publishers, Inc., New York, N.Y., 1989, 393–425), phthalocyanines are generally thought of as being hemolytic, making applicants' results herein all the more surprising. For example, Ben-Hur and Rosenthal ("Photohemolysis of Human Erthrocytes Induced by Aluminum Phthalocyanine Tetrasulfonate", Cancer Lett., 30: 321–327, 1986) studied the photohemolysis of human red blood cells induced by aluminum phthalocyanine tetrasulfonate. Substantial (20–100%) hemolysis was induced by treatment with 2.5 to 10 $\mu$M AlPCS$_4$ at all light fluences $\geq 40$ KJ/m$^2$ ($\geq 4$ J/cm$^2$). Ben-Hur and Rosenthal did not address the problem of virus kill. Similarly, Sonoda, Krishna and Riesz ("The Role of Singlet Oxygen in the Photohemolysis of Red Blood Cells Sensitized by Phthalocyanine", Photochem. Photobiol., 46: 625–631, 1987) studied the photohemolysis induced by each of several phthalocyanine derivatives. Aluminum and zinc phthalocyanines were each hemolytic, while free (no metal) phthalocyanine or those with iron, copper or cobalt as the central metal cation were not. Virus kill was not studied.

Singer et al (C. R. J. Singer, T. Azim and Q. Sattentau, "Preliminary Evaluation of Phthalocyanine Photosensitization For Inactivation Of Viral Pathogens in Blood Products", [abstract] British J. Hematology, Mar. 23–25, 1988:Abs. 31), in what is believed to be the only study on virus kill performed with phthalocyanines, demonstrated that an unstated quantity of both Epstein Barr virus and of HIV added to plasma was inactivated on treatment with 5 and 25 $\mu$g/mL of sulfonated aluminum phthalocyanine and 2 mW/cm$^2$ for 30 minutes (3.6 J/cm$^2$). Factor VIII recovery was only 50%. Singer et al reported no actual work on cells or cell-associated virus, though they state that application to red cells is being evaluated. Given the relatively poor recovery (50%) of factor VIII reported by Singer, the greater fragility of cells than proteins, and the previous experience on the photohemolysis of red cells to treatment with phthalocyanine, the results herein are all the more surprising.

Other Lipophilic Dyes in the Treatment of Whole Blood or Red Blood Cell Concentrates Cole et al (Cole, M., Stromberg, R., Friedman, L., Benade, L., Shumaker, J., "Photochemical Inactivation of Virus in Red Cells", Transfusion, 29, Supp:42s Abs., 1989) explored the use of merocyanine 540 in the treatment of packed red blood cells diluted to a hematocrit of 15%. When plasma was removed such that its concentration was 2.6%, a 6 log reduction of vesicular stomatitis virus was achieved. However, only a 1 log reduction in VSV was achieved in samples containing 15% plasma. The authors concluded that "although plasma is required to protect the red blood cells from damage, viral kill is also significantly reduced". This conclusion is supported by the observation that the presence of 5% albumin inhibited virus kill in suspension of washed platelets (Prodouz, K. N., "Effect of Merocyanine 540 on Platelet Function and Reduction of its Antiviral Activity by Albumin", Transfusion, 29, Supp:42s Abs., 1989), and that though 6 logs of model viruses in buffer could be inactivated by merocyanine 540, only 1–3 logs of virus could be inactivated in the presence of 12–25% plasma (Moroff, G., Benade, L. E., Dabay, M., George, V. M., Shumaker, J. and Dodd, R. Y., "Use of Photochemical Procedures to Inactivate Viruses in Platelet Suspensions", Transfusion, 29, Supp:S15 Abs., 1989). Furthermore, the authors stated that the procedure "adversely affected platelet properties".

Matthews, J. T., Newman, J. T., Sogandares-Bernal, F., et al, "Photodynamic Therapy of Viral Contaminants with Potential For Blood Banking Applications", Transfusion, 1988;28:81–83 studied treatment of whole blood with hematoporphyrin derivatives and light. They reported the inactivation of $3 \times 10^5$ PFU of herpes simplex virus type 1 (HSV-1) on treatment of culture medium with 2.5 µg/mL dihematoporphyrin ether (DHE) and light, but only the inactivation of $10^3$ PFU on treatment of blood under the same condition. Increasing the concentration of DHE to 20 µg/ml did not improve virus kill. While red blood cell structure and function was well maintained at 2.5 µg/mL DHE and light at 5 J/cm², cell-free HIV ($2 \times 10^3$ $ID_{50}$) added to buffer alone was not completely killed under this condition.

Other Photoactive Compounds

Lin et al (Lin, L., Wiesehahn, G. P., Morel, P. A. and Corash, L., "Use of 8-Methoxypsoralen and Long-wavelength Ultraviolet Radiation for Decontamination of Platelet Concentrates", Blood, 74:517–525, 1989) demonstrated that psoralen and exposure to UV-A inactivated $\geq 10^{5.5}$ID of feline leukemia virus added to a platelet concentrate; however, studies in whole blood or red cell concentrates were not performed. Platelet morphology, aggregation, and the release reaction were well maintained immediately following treatment, and showed comparable values when compared to untreated controls on storage for up to 96 hours. In contrast, Moroff et al (Moroff G., Benade, L. E., Dabay, M., George, V. M., Shumaker, J. and Dodd, R. Y., "Use of Photochemical Procedures to Inactivate Viruses in Platelet Suspensions", Transfusion, 29, Supp, S15 Abs., 1989) explored the use of psoralen for the treatment of platelets and concluded that the presence of as little as 12% plasma inhibited virus kill and that platelet properties were adversely affected. It should be pointed out that, as typically prepared, red blood cells and platelet concentrates for transfusion are suspended in 100% plasma.

Other Agents

In U.S. patent application Ser. No. 07/279,179, filed Dec. 2, 1988, and in a recent published abstract (Williams et al, Blood, 1988, 72: Suppl.:287a), vesicular stomatitis virus added to whole blood was reported to be inactivated on incubation with a hydrolyzable, aryl diol epoxide without causing red cell lysis.

Ozone has been asserted to decontaminate whole blood containing $10^9$ pFU/mL of hepatitis virus (Zee, Y. C. and Bolton, D. C., "Ozone Decontamination of Blood and Blood Products", U.S. Pat. No. 4,632,980). However, no data were provided in support of this allegation.

Prodouz, K. N., Fratantoni, J. C., Boone, J. E. and Bonner R. F., "Use of Laser-UV for Inactivation of Virus in Blood Products", Blood, 1987; 70:589–592 reported that laser-UV treatment of a platelet concentrate largely maintained platelet function under conditions where up to $10^6$ ($ID_{50}$) of polio virus was inactivated. However, virus inactivation was studied in buffered medium alone and not in the presence of platelets, and only a cell-free form of the virus was employed.

Hartman et al (Hartman, F. W., Mangun, G. H., Feeley, N., Jackson, E., "On the Chemical Sterilization of Blood and Blood Products", Proc. Soc. Exp. Biol. Med., 70:248–254, 1949) showed that treatment of whole blood with the nitrogen mustard, methyl-bis(beta-chloroethyl) amine hydrochloride resulted in the inactivation of $10^{6.6}$ $ID_{50}$ of vesicular stomatitis virus under conditions where red cell hemolysis was not greater than the control. It should be pointed out that nitrogen mustards are carcinogens.

LoGrippo (LoGrippo, G. A., "Investigations of the Use of Beta-Propiolactone in Virus Inactivation", Ann. NY Aca. Sci., 83, 578–594, (1959)) treated red cells separately from plasma with beta-propiolactone. Treatment resulted in the inactivation of more than $10^8$ $ID_{50}$ of Eastern equine encephalitis virus without causing red cell hemolysis. Subsequent injection of the treated red cells in man resulted in a shortened circulatory half-life.

SUMMARY OF THE INVENTION

It is an object of the present invention to inactivate viruses in cell-containing compositions without incurring substantial disruption or inactivation of cells.

It is another object of the present invention to inactivate viruses in whole blood, red blood cell concentrates and platelet concentrates, without adversely affecting red cell or platelet structure or function.

It is another object of the present invention to inactivate viruses in biological compositions without incurring substantial inactivation of desired, soluble biological substances (e.g., coagulation factor concentrates, hemoglobin solutions).

It is a further object of this invention to improve virus safety in blood banks of both whole blood, red blood cell concentrates and platelet concentrates, and any products derived from whole blood, red blood cell concentrates or platelet concentrates.

It is still a further object of the invention to reduce exposure to hospital care workers and other health care workers to viruses to which they otherwise would be exposed.

It is still a further object of the invention to reduce the circulating viral burden in animals and man.

It is still a further object of the invention to improve the storage properties of cell-containing compositions, e.g., red cell concentrate, prior to use.

The above objects, as well as other objects, aims and advantages are satisfied by the present invention.

The present invention concerns a method of inactivating excellular lipid enveloped human pathogenic viruses or intracellular human pathogenic viruses in a cell-containing composition without incurring substantial disruption or inactivation of cells, comprising contacting a cell-containing composition having $\geq 1 \times 10^9$ cells/ml and containing infectious virus with a virucidally effective amount of at least one photoreactive compound having an absorption maximum of $\geq 630$ nm, light and an oxidizer to substantially inactivate the virus and to result in a retention of intact cell functionality and structure of greater than 80%.

In accordance with another aspect of the invention, extracellular and intracellular virus in a biological composition is inactivated without incurring substantial disruption or inactivation of the composition, by a process comprising contacting said composition with a virucidally effective amount of at least one photoreactive compound, light, and a quencher thereby to inactivate said virus while retaining functionality of said substance.

More particularly, the present invention concerns a method for inactivating extracellular as well as intracellular viruses in whole blood, red blood cell concentrates, platelet concentrates or products derived from whole blood or red blood cell concentrates or platelet concentrates comprising contacting said whole blood, red blood cell concentrates or products derived from whole blood or red blood cell concentrates with an effective virucidal amount of a photoreactive compound having an absorption maximum greater than 630 nm, for example, a purpurin or a phthalocyanine, and exposing the resultant composition to light in the presence of an oxidizer, together with the optional presence of a quencher, for example, glutathione.

The present invention also concerns a composition comprising human red blood cells suitable for transfusion at concentration of $\geq 1$ to $10^9$ cells/ml and having all extracellular lipid enveloped and intracellular human pathogenic viruses in a non-infectious form, the red cells preferably having a normal recovery on infusion of 70% or greater, preferably 85% or greater and having a satisfactory circulatory survival, e.g., for red blood cells of $\geq 20$ days and preferably for 30 days.

The aforesaid compositions preferably have a greater resistance to osmotic shock than normal.

BRIEF DESCRIPTION OF THE DRAWINGS

FIG. 1 comprises four graphs depicting the inactivation of cell-free vesicular stomatitis virus (VSV) with aluminum phthalocyanine chloride (AlPc).

FIG. 2 comprises four graphs depicting the inactivation of cell-free VSV with sulfonated aluminum phthalocyanine.

DETAILED DESCRIPTION OF THE INVENTION

Blood is made up of solids (cells, i.e., erythrocytes, leucocytes, and platelets) and liquid (plasma). The cells are transfused in the treatment of anemia, clotting disorders, infections, etc. In addition, the cells contain potentially valuable substances such as hemoglobin, and they can be induced to make other potentially valuable substances such as interferon, growth factors, and other biological response modifiers. The plasma is composed mainly of water, salts, lipids and proteins. The proteins are divided into groups called fibrinogens, serum globulins and serum albumins. Typical antibodies (immune globulins) found in human blood plasma include those directed against infectious hepatitis, influenza H, etc.

Blood transfusions are used to treat anemia resulting from disease or hemorrhage, shock resulting from loss of plasma proteins or loss of circulating volume, diseases where an adequate level of plasma protein is not maintained, for example, hemophilia, and to bestow passive immunization.

With certain diseases one or several of the components of blood may be lacking. Thus the administration of the proper fraction will suffice, and the other components will not be "wasted" on the patient; the other fractions can be used for another patient. The separation of blood into components and their subsequent fractionation allows the cells and/or proteins to be concentrated, thus enhancing their therapeutic use.

Cell types found in human blood include red blood cells, platelets and several types of leukocytes. Methods for the preparation of cell concentrates useful in transfusion can be found in *Kirk Othmer's Encyclopedia of Chemical Technology*, Third Edition, Interscience Publishers, Volume 4, pp 25–37, the entire contents of which are incorporated by reference herein.

Proteins found in the blood cell fraction include hemoglobin, fibronectin, fibrinogen, platelet derived growth factor, superoxide dismutase, enzymes of carbohydrate and protein metabolism, etc. In addition, the synthesis of other proteins can be induced, such as interferons and growth factors.

A comprehensive list of inducible leukocyte proteins can be found in Stanley Cohen, Edgar Pick, J. J. Oppenheim, "Biology of the Lymphokines", Academic Press, New York, (1979).

The present invention is directed to contacting at least one photoreactive compound with a cell-containing composition such as whole blood, red blood cell concentrates, platelet concentrates, platelet extracts, leukocyte concentrates, semen, ascites fluid, milk, lymphatic fluid, hybridoma cell lines and products derived from any of the above.

The present invention can be employed to treat the product of a composition containing a non-blood normal or cancerous cells or the product of gene splicing.

When quenchers are not added, suitable photosensitizer compounds for use in the present invention include phthalocyanines, purpurins and other molecules which resemble the porphyrins in structure, although some of the atoms in the basic porphyrin-like frame (as well as their arrangement) may vary. For example, phthalocyanines are porphyrin-like (azaporphyrins), except that the tetrapyrrole ring linked by methine carbon atoms in porphyrins is replaced by four isoindole units linked by aza nitrogen atoms. These phthalocyanine, porphyrin, and purpurin molecules may or may not contain metallo or metalloid central atoms, and various substitutents may be placed on the basic molecular framework to (a) red-shift the longest wavelength absorption maxima beyond 630 nm, (b) increase the molar extinction coefficient to enhance the absorptivity of the exciting red light, and (c) modulate the solubilities of the photosensitizer molecules in aqueous environments, as well as their lipophilicities, or DNA-binding abilities.

Photoreactive compounds for use in the present invention which contain metals, for example, germanium or gallium, are diamagnetic, rather than paramagnetic.

Photosensitizers, including substituted photosensitizers, which can be utilized in the present invention will result in compounds having the following characteristics:

(a) a molar extinction coefficient of $\geq 50,000$ Molar$^{-1}$ cm$^{-1}$;

(b) an absorption maximum of $\geq 630$ nm, preferably 660 to 730;

(c) a solubility of $\geq 1$ $\mu$M in both water and apolar solvents;

(d) having amphiphilic characteristics;

(e) soluble in aqueous saline buffer solutions at the concentrations of use in a time frame of approximately 2 hours.

Preferred photoreactive compounds for use in the present invention are phthalocyanines (Pc's or PC's). Phthalocyanines are porphyrin-like compounds which are chemically stable, well defined, and easily synthesized (Spikes, J., "Phthalocyanines as Photosensitizers in Biological Systems and for the Photodynamic Therapy of Tumors", *Photochemistry and Photobioloqy*, 1986;43:691–699 and Ben-Hur, E. and Rosenthal, I., "The Phthalocyanines: A New Class of Mammalian Cells Photosensitizers with a Potential for Cancer Phototherapy", *Int. J. Radiat. Biol.*, 1989;47:145–147). There is encouraging evidence in the literature indicating the lack of toxicity of phthalocyanine dyes to mammals (Moser, F. H. and Thomas, A. C., *The Phthalocyanines*, Boca Raton-:CRC Press, 1984). The phthalocyanines have very strong electronic absorption bands at wavelengths above 630 nm. Hemoglobin has a relatively low absorbance in this spectral region.

Non-limiting examples of phthalocyanines for use in the present invention include the following:

zinc tetrasulfophthalocyanine, tetrasulfophthalocyanine, aluminum tetranitrophthalocyanine, zinc-tetranitrophthalocycyanine, tetracarboxyphthalocyanine, GaCl-tetrasulfophthalocyanine, AlCl-tetrasulfophthalocyanine, Ga-tetrasulfophthalocyanine and GaCl-, AlCl- or Ga-tetranitrophthalocyanine.

In a preferred embodiment of the invention, aluminum phthalocyanines are employed. Preferred aluminum phthalocyanines include aluminum phthalocyanine chloride (AlPc) and sulfonated forms of aluminum phthalocyanine, e.g., AlPcS$_2$ and AlPcS$_4$. Zinc can replace aluminum as the central atom, and the ring can be nitrated instead of sulfonated.

When quenchers are added, suitable photosensitizer compounds for use in the present invention include phthalocyanines, purpurins, and other molecules which resemble the porphyrins in structure (as described above) as well as photoactive compounds excited by ultraviolet light (e.g., psoralen, 8-methoxypsoralen, 4'-aminomethyl-4,5',8-trimethyl psoralen, bergapten, and angelicin), and dyes which absorb light in the visible spectrum (e.g., hypericin methylene blue, eosin fluoresceins and flavins).

Suitable quenchers are any substances known to react with free radicals or reactive forms of oxygen, more specifically which decrease the efficiencies of photodynamically catalyzed chemical reactions (e.g. DNA strand breads), or decrease the cytoxicity in photodynamic cell killing experiments. In accordance with the present invention, however, surprisingly quenching is effected without substantial decrease in virucidal action.

Representative quenchers include unsaturated fatty acids, reduced sugars, cholesterol, indole derivatives, and the like, azides, such as sodium azide, tryptophan, polyhydric alcohols such as glycerol and mannitol, thiols such as glutathione, superoxide dismutase, quercetin, DABCO, and the like. The use of mixtures of quenchers is also contemplated.

The quencher is used in conventional quenching amounts but surprisingly, when used, the overall process results in preferential damage to the virus but not the desired biological material.

Non-limiting examples of lipid coated, human pathogenic viruses that can be inactivated by the present invention include vesicular stomatitis virus (VSV), Moloney sarcoma virus, Sindbis virus, human immunodeficiency viruses (HIV-1; HIV-2), human T-cell lymphotorophic virus-I (HTLV-I), hepatitis B virus, non-A, non-B hepatitis virus (NANB) (hepatitis C), cytomegalovirus, Epstein Barr viruses, lactate dehydrogenase elevating virus, herpes group viruses, rhabdoviruses, leukoviruses, myxoviruses, alphaviruses, Arboviruses (group B), paramyxoviruses, arenaviruses and coronaviruses. Non-limiting examples of non-enveloped viruses that can be inactivated by the present invention include parvirus, polio virus, hepatitis A virus and enteric non-A, non-B hepatitis virus.

The process of the present invention is preferably conducted at 0 to 45° C., and most preferably at 4 to 37° C. for up to 48 hours and preferably for 2 to 24 hours.

The process of the invention is preferably conducted in a neutral pH range of 6.3 to 7.7. A typical light fluence range for the invention is 5 to 500 J/cm$^2$, preferably 100 to 500 J/cm$^2$ with phthalocyanine and 5 to 100 J/cm$^2$ with psoralen. The brighter the light, the less time is required. With flowing systems, very bright light for short times would be employed. For blood bags, longer times and less bright light can be used.

Preferably the concentration of the photoreactive compound in the absence of quenchers is 1 to 100 $\mu$M; for red cell concentrates, the concentration of the photoreactive compound is most preferably 10 to 25 $\mu$M. When quenchers are used, the concentrations of photoactive compounds are those typically employed, e.g. 25 $\mu$g/ml for AMT.

The process of the present invention is carried out in the presence of an oxidizer. Oxygen is a nonlimiting example of an oxidizer for use in the present invention. The concentration of oxygen can be the endogenous quantity, or can be modified by placement of the material being treated in an atmosphere designed to lower or raise oxygen concentration.

Cell-containing compositions to be treated according to the invention have $\geq 1 \times 10^9$ cells/ml, preferably $\geq 5 \times 10^9$ cells/ml and most preferably $\geq 1 \times 10^{10}$ cells/ml. Furthermore, cell-containing compositions to be treated according to the invention have preferably $\geq 4$ mg/ml protein and more preferably $\geq 25$ mg/ml protein and most preferably 50 to 60 mg/ml protein (unwashed cells).

Non-cell containing compositions to be treated according to the invention have $\geq 0.1$ mg/ml and preferably $\geq 5$ mg/ml protein.

In the inventive process, at least $10^4$, preferably $10^6$, infectious units of virus are inactivated.

The inventive process results in improved storage stability, i.e., treated cells that can be stored in liquid or frozen form and for which reduced cell destruction is obtained.

The cell-containing composition according to the invention, while initially containing ≧1000 infectious units of virus/L, after the virus has been inactivated and treatment according to the invention has been conducted, has a retention of intact cell functionality and structure of greater than 80%, preferably greater than 90% and most preferably greater than 98%.

By the inactivation procedure of the invention, most if not virtually all of the viruses contained therein would be inactivated. A method for determining infectivity levels by inoculation into chimpanzees (in vivo) is discussed by Prince, A. M., Stephen, W., Bortman, B. and van den Ende, M. C., "Evaluation of the Effect of Beta-propiolactone/Ultraviolet Irradiation (BPL/UV) Treatment of Source Plasma on Hepatitis Transmission by Factor IX Complex in Chimpanzees", *Thrombosis and Hemostasis*, 44: 138–142, (1980).

According to the invention, inactivation of virus is obtained to the extent of at least "4 logs", preferably ≧6 logs, i.e., virus in the sample is totally inactivated to the extent determined by infectivity studies where that virus is present in the untreated sample in such a concentration that even after dilution to $10^4$ (or $10^6$) viral activity can be measured.

The present invention describes inactivating viruses, while simultaneously retaining labile blood cell functional and structural features.

Functional activities of red cells are ascertained by measurements of metabolite levels, enzymatic activities, electrolyte levels and oxygen carrying capacity. Structural integrity of red cells is assessed by measurements of hemoglobin release, osmotic fragility, survival in vivo following radiolabeling with chromium-51, antigenicity and by evaluation of modification of cell surface proteins.

Functional activities of platelets are determined by their ability to aggregate in the presence of certain biological agents and their morphology. Structural integrity of platelets is assessed by in vivo survival following radiolabeling with indium-11 and identification of the presence of specific platelet antigens.

The method of the present invention can be used in conjunction with other viral inactivating agents, e.g., beta-propiolactone or UV or other forms of radiation, e.g., gamma rays.

The present invention demonstrates the following:
(1) photoreactive compounds such as phthalocyanines together with light exposure can inactivate viruses in whole blood or red cell concentrates, without adversely affecting red cell structure or function,
(2) a lipophilic dye with an absorption maximum of ≧630 nm can inactivate large quantities (e.g., $\geq 10^{5.5} ID_{50}$) of virus in whole blood or a red cell concentrate under conditions which maintain red cell structure and function,
(3) both extracellular and intracellular virus present in whole blood, a red cell concentrate or a platelet concentrate can be inactivated without adversely affecting cell structure or function, and
(4) a lipophilic dye on exposure to light can stabilize red blood cells to osmotic injury.
(5) the inclusion of a quencher of a photochemically catalyzed reaction during or following said reaction reduces cell or protein damage which may occur without substantially reducing virus kill.

The principal advantage of the phthalocyanines over other lipophilic dyes such as hematoporphyrin derivative is the extremely strong optical absorption of phthalocyanines at 630–700 nm. Light at this wavelength has improved tissue penetrating properties, as compared with the shorter wavelength of light absorbed by the usual porphyrin and hematoporphyrin sensitizers. Furthermore, the absorption spectrum of phthalocyanines is better separated from that of blood components, especially hemoglobin, which has an absorption maximum at 578 nm.

As reported herein, photocatalyzed reactions with hydrophobic dyes results in inactivation of extracellular enveloped viruses such as VSV and HIV, while extracellular encephalomyocarditis virus (EMC), a non-enveloped virus, was not inactivated. In addition, $AlPcS_2$ and $AlPcS_4$, which bind to the more hydrophilic regions of the cell, were more effective virucidal agents than AlPc at a similar concentration. It is important to note that both cell-free and cell-associated viruses were inactivated under the conditions examined, and that red cell integrity was maintained, as judged by the absence of hemoglobin release (<2%) on treatment, or following storage. In fact, treatment of a red cell suspension with AlPc and light stabilized the red cell against hypotonic shock. Further evidence of the integrity of $AlPcS_4$-treated red blood cells comes from the measurement of their circulatory half-life. Treated baboon red blood cells had a half-life of 13.4 days while untreated baboon red blood cells had a half-life of 13.9 days.

That VSV added to an entire red blood cell concentrate unit was inactivated indicates that a procedure based on AlPc addition and exposure to light can be implemented in a blood banking environment. Treatment of collected units in a light cabinet, perhaps for a period as long as 6 to 24 hours, or for briefer periods if multiple or more intense light sources are employed, is envisioned.

In a preferred embodiment of the present invention, a light fluence of 250 to 1000 $J/cm^2$ is applied to a sample 2 to 4 cm thick and agitation is utilized. In a further preferred embodiment of the invention, the process according to the invention is applied to a sample in a blood bag.

After treatment with the photoreactive compound, excess photoreactive compound can be removed by centrifugation, washing and/or dialysis.

In an embodiment of the present invention, the treated cell-containing fraction from the inventive process is transfused or returned to the donor, e.g., human donor, from which the initial cell-containing fraction was derived. In this manner, the level of circulating virus in the donor will be reduced, thus improving the donor's ability to clear virus and/or improving the efficacy of antiviral drugs.

As noted hereinabove, the invention also extends to an inactivation method involving a photoactive compound, light and a quencher, with or without an oxidizer.

The inclusion of a quencher during AMT/UVA treatment of a platelet concentrate in the presence of oxygen resulted in normal platelet function, as measured in standard aggregation reaction, and the inactivation of $\geq 10^{5.5}$ $TCID_{50}$ of VSV; without quencher addition, the rate and extent of platelet aggregation was reduced. Surprisingly, virus kill was similar in both samples. Similarly, the inclusion of a quencher during AMT/UVA treatment of blood plasma resulted in the quantitative recovery of coagulation factor VIII; without quencher addition, the recovery was only 77%. Again, surprisingly, there was no difference in VSV kill. In yet another example, the circulatory half-life of rabbit red blood cells was assessed following treatment with aluminum phthalocyanine tetrasulfonate and visible light. Without adversely affecting virus kill, inclusion of a quencher resulted in prolongation of the circulatory survival of treated red blood cells.

The invention will now be described with reference to the following non-limiting examples.

EXAMPLES

Materials and Methods

Blood

Whole blood was typically less than 48 hours old when used. Prior to use, it was stored at 4° C. Red blood cell concentrates (RBCC) were prepared from whole blood by centrifugation for 20 minutes at 2000 r.p.m. with removal of most of the plasma layer. Where indicated, whole blood was diluted 5-fold or the red blood cell concentrates were diluted 2-fold with phosphate buffered saline (PBS; Gibco Laboratories, Grand Island, N.Y.).

Aluminum Phthalocyanine Solutions

Aluminum phthalocyanine chloride (AlPc) was purchased from Kodak Laboratory Chemicals, Rochester, N.Y. Stock solutions of AlPc (0.01M) were prepared in spectrophotometric grade N,N-dimethylformamide (Aldrich, Milwaukee, Wis.). Aluminum phthalocyanine tetrasulfonate (AlPcS$_4$) and aluminum phthalocyanine disulfonate (AlPcS$_2$) were purchased from Porphyrin Products Inc., Logan, Utah. Stock solutions of AlPcS$_2$ and AlPcS$_4$ ($6.2\times10^{-4}$ M) were prepared in PBS. The concentration of all phthalocyanine solutions was determined spectro-photometrically using a molar extinction coefficient of $2\times10^5$ 1 mol$^{-1}$ cm$^{-1}$ at the absorption maximum at 670 nm for AlPc, 674 nm for AlPcS$_2$ and 675 nm for AlPcS$_4$.

Psoralen Solutions

4'-aminomethyl-4,5',8-trimethylpsoralen (AMT) was purchased from HRI Assoc. Inc., Concord, Calif. Stock solutions of AMT (4 mg/ml) were prepared in distilled water.

Model Virus Studies

The inactivation of the following viruses was studied: vesicular stomatitis virus (VSV), a lipid enveloped, RNA virus; encephalomyocarditis virus (EMC), a protein enveloped, RNA virus; and human immunodeficiency virus (HIV), a human, pathogenic retrovirus.

VSV was cultured in human A549 cells. EMC stocks were prepared in mouse L929 or human A459 cells. Culturing and assay procedures were similar to those described in Horowitz, B., Wiebe, M. E., Lippin, A. and Stryker, M. H., "Inactivation of Viruses in Labile Blood Derivatives", *Transfusion*, 1985;25:516–522. Infectivity of VSV and EMC was assessed by endpoint, 10-fold serial dilutions in DMEM culture medium (Gibco Laboratories, Grand Island, N.Y.) with 10% fetal calf serum (FCS; MA Bioproducts, Walkersville, Md.). Each dilution was used to inoculate eight replicate wells of human A549 cells in 96-well microtiter plates. Virus-induced cytopathology was scored after 72 hours of incubation at 37° C. in 5% $CO_2$. The reported virus titer was calculated using the Spearman-Karber method (Spearman, C., "The Method of Right and Wrong Cases' ('Constant Stimuli') Without Gauss's Formula", *Br. J. Psychol.*, 1908;2:227–242) and indicates the quantity of virus which infect s 50% of the tissue culture wells (TCID$_{50}$).

Cell-associated VSV was prepared by incubating a confluent monolayer of humanA549 cells with 5 ml of $10^7$ ID$_{50}$/ml VSV in serum-free DMEM for 1 hour at 37° C. under 5% $CO_2$ in 150 cm$^2$ tissue culture flasks. The multiplicity of infection under these conditions was approximately 2.1 TCID$_{50}$/cell. After decanting off the liquid, the attached cells were washed three times to remove free virus with 50 ml PBS per wash. Afterwards, 40 ml of DMEM containing 5% FCS were added, and the cells were incubated for an additional 4 ¾ hours. The attached cells were washed three times with PBS and released by treatment for 10 minutes with a normal saline solution containing 0.01% trypsin (Cooper Biomedical, Freehold, N.J.; two times crystallized) and 5 µg/ml EDTA. The released cells were collected by centrifugation, washed three times with PBS and resuspended in PBS.

To assess inactivation, cell-free virus was added to the blood component being studied at a 1:10 dilution, and 3 ml aliquots of this mixture were distributed in polystyrene tubes (Fisher Scientific, Springfield, N.J.; Cat. #2027; 7 ml capacity) followed by the addition of the phthalocyanine derivative. The samples were mixed continuously using a hematology mixer (Fisher Scientific, Cat. #14–060–1) and photoirradiated with light from a Solar Simulator (Oriel Corp., Stratford, Conn.) fitted with a Zenith 300 watt Xe short arc lamp equipped with an amber, 570 nm long-pass filter (Oriel Corp.). The light power at the sample was about 25–26 mWatts/cm$^2$ as measured with a photometer (Model No. IL1350 International Light, Newburyport, Mass.) with a detector (Model No. SED038) fitted with a wide band pass filter (F#8174) and a diffuser (W#4425). As compared with the data presented below, the filtration through a 676 nm interference filter (the Optometrics Corp., Catalog No. 02–6765, Ayer, Mass.) placed on the detector permitted the transmission of 1.3% of the light power. Irradiation times were typically 30, 60 and 120 minutes corresponding to fluences of 44, 88 and 176 J/cm$^2$ respectively. A constant flow of air was provided by a fan, and the temperature of the sample did not rise above 28° C. during irradiation.

Virus inactivation of an entire red blood cell concentrate (RBCC) unit was carried out in a 600 ml capacity #5J359 bag (Fenwall Division, Deerfield, Ill.). A Thermolyne Specimix mixer model M26125 (Sybron Corp., Iowa) was used to mix the sample in the bag during photoirradiation.

For assessment of virus inactivation, the reaction was stopped by 10-fold dilution into DMEM containing 5% fetal calf serum, and the red blood cells were removed by centrifugation at 1500 rpm for 10 minutes. The lack of virus inactivation at this dilution or in the absence of light was confirmed for each of the inactivation conditions studied. Samples were sterile filtered (Swinnex filters, Millipore Corp., Bedford, Mass.) and frozen at -70° C. or below until assay.

The procedures for the assessment of the inactivation of cell-associated VSV were similar to those of cell-free VSV, except all experiments with cell-associated VSV were carried out under totally controlled aseptic conditions. At the conclusion of the experiment, the infected A549 cells were isolated with the addition of Ficoll-Paque (Pharmacia Fine Chemicals, Piscataway, N.J.) and centrifuged in a swinging bucket rotor at 1800 xg for 30 minutes at ambient temperature. The layer containing the A549 cells was collected, washed three times with PBS by centrifugation, resuspended in 1 ml PBS and immediately assayed for VSV infectivity by endpoint, 10-fold serial dilutions as with cell-free virus.

Assessment of HIV Inactivation

The HTLV III$_b$ strain of human immunodeficiency virus (HIV) was used in these experiments. Measurement of infectivity was similar to that reported previously (Prince, A. M., Pascual, D., Kosolapov, L. B., et al, "Prevalence, Clinical Significance, and Strain Specificity of Neutralizing Antibody to the Human Immunodeficiency Virus", *The Journal of Infectious Diseases*, 1987;156:268–272). Ten thousand-fold concentrates of cell-free HIV, prepared by continuous flow sucrose banding, were purchased from Bionetics, Inc. (Rockville, Md.). Titrations were carried out with serial, ten-fold dilutions in microtiter plates using RPMI 1640 containing 10% FCS, with either CEM or H9 cells at a concentration of $8 \times 10^5$/mL. Before use, cells were conditioned by incubation for 1 hour at 37° C. in the above medium containing 2 µg/mL of polybrene. Virus in treated samples was adsorbed to cells for 2 hours at 37° C. in the dark. Cultures were then washed twice in medium by centrifuging plates for 10 minutes at 2000 rpm and aspirating the supernatants in order to remove the treating compound and reduce toxicity. 150 µl cultures were then fed with 25 µl of medium at 4, 7 and 10 days. At 14 days, cultures were washed twice with PBS (phosphate buffered saline) to remove viral antigens carried over from the inoculum, and the cells were lysed in PBS containing 0.5% Triton X-100. Lysates were assayed for HIV p55 antigens by ELISA using plates coated with rabbit antiserum against recombinant p55 (Syntex Corp., Palo Alto, Calif.) and peroxidase labeled rabbit anti-p55. This assay had essentially the same sensitivity in measurement of p24 as the Dupont p24 antigen assay.

To increase the sensitivity for measurement of small quantities of residual virus, 0.5–1.0 ml of undiluted virus-containing fluids treated with AlPc were also inoculated into 5 ml macro-cultures, and were fed by removing half volumes and replacing with fresh medium twice weekly for 4 weeks.

For cell-associated HIV, 25 ml culture of $8 \times 10^5$/mL CEM of H9 cells were inoculated with $10^4$ TCID$_{50}$ of HIV. Cultures were fed by removal of half volumes and replacement with fresh medium twice weekly. At each feeding, supernatant fluids were assayed for p55 antigens by ELISA. When the titer reached 1:64 or greater, usually at 10–12 days, the infected cells were used in the following experiments. Prior to use in experiments, aliquots of $10^6$ infected cells were pelleted and resuspended in 100 µL of HIV immune globulin (Prince, A. M., Horowitz, B., Baker, L. et al, "Failure of an HIV Immune Globulin To Protect Chimpanzees Against Experimental Challenge With HIV", *PNAS*, 1988;85:6944–6948), incubated for 1 hour at 37° C., and washed three times in culture medium in order to reduce the amount of non-cell associated virus. Infected cells were then suspended in medium, or whole blood anticoagulated with CPD (citrate phosphate dextrose), to a concentration of $10^6$/mL. These mixtures were exposed to varying concentrations of AlPc with or without exposure to light. After treatment, samples were diluted 1:2 with RPMI-1640 and centrifuged through Ficoll-Hypaque to separate lymphocytes from erythrocytes. The recovered lymphocytes were washed three times, counted, and serially diluted in 100 µl of medium. Uninfected CEM cells were then added and the cultures processed as for the infectivity titration described above.

Red Cell Measurements

Total hemoglobin was quantitated using Drabkin's reagent (Sigma Procedure No. 525, Sigma Diagnostics, St. Louis, Mo.). Plasma hemoglobin was assessed, after removal of cells by centrifugation, by measuring the optical density of the plasma at A540 and assuming an absorbance of 0.86 for a 1 mg/ml solution (Antonini, E. and Brunori, M., "Hemoglobin and Myoglobin in Their Reactions with Ligands", Amsterdam: North-Holland Publishing Co., 1971. (Neuberger A., Tatum E. L., eds., *Frontiers of Biology*; Vol. 21)). Prior to centrifugation, red cell concentrates were diluted 1:1 with PBS. The results were expressed as a percentage of the total hemoglobin present. Osmotic fragility of treated red blood cells was measured as previously described in Dacie, J. V., Lord, M. B., Vaughan, J. M. and Oxon, D. M., "The Fragility of Red Blood Cells, Its Measurements and Significance", *J. Path Bact.*, 1938, 46:341–356. pH measurements were made with a PHM 82 pH meter (Radiometer America Inc., Cleveland, Ohio). The circulatory half-life of autologous rabbit red blood cells was determined by washing the treated red blood cells to remove plasma proteins and labeling the cells with $^{51}$Cr.

Example 1
Inactivation of VSV and EMC By AlPc

The inactivation of cell-free VSV added to whole blood ($5 \times 10^9$ red blood cells/ml) or a red cell concentrate ($1 \times 10^{10}$ red blood cells/ml) in the presence of AlPc was dependent on its concentration and the fluence (dosage) of light (FIG. 1). Cell-free VSV and AlPc at the indicated concentration were added to whole blood (FIG. 1a), a red blood cell concentrate (FIG. 1b), whole blood diluted 5-fold with PBS (FIG. 1c) and a red blood cell concentrate diluted 2-fold with PBS (FIG. 1d). The plasma protein concentration in whole blood and the red cell concentrate was 60 mg/mL prior to the dilution indicated. Samples (3 mL) were exposed to a constant intensity of light (25–26 mWatts/cm$^2$) for a varying duration such that the total light fluence was 44 J/cm$^2$ (closed circles), 88 J/cm$^2$ (open circles), or 176 J/cm$^2$ (open triangles). Following exposure to light, virus infectivity was assessed as described herein.

Figure 1A:
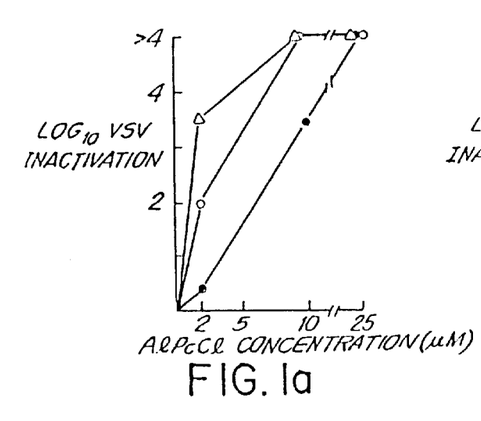
FIG. 1a depicts the results using whole blood.
Figure 1B:
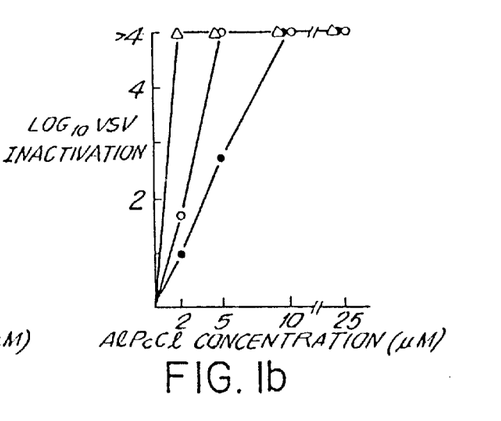
FIG. 1b depicts the results using a red blood cell concentrate.
Figure 1C:
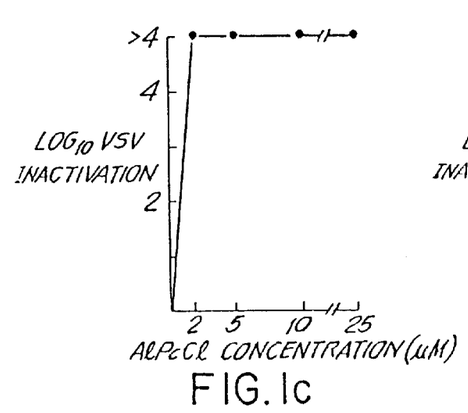
FIG. 1c depicts the results using whole blood diluted 5-fold with PBS.
Figure 1D:
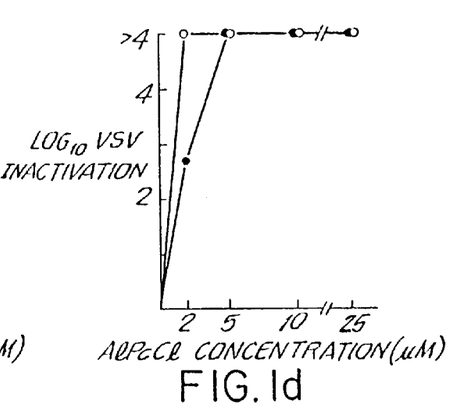
FIG. 1d depicts the results using a red blood cell concentrate diluted 2-fold with PBS.

Complete inactivation of VSV ($\geq 10^{4.0}$ to $10^{4.5}$ TCID$_{50}$) added to whole blood was observed at an AlPc concentration of 10 AM and a light fluence of 88 and 176 J/cm$^2$, corresponding to a light intensity of 25 mwatts/cm$^2$ and exposure times of 60 and 120 minutes, respectively. At a fluence of 44 J/cm$^2$, complete inactivation of added VSV required an AlPc concentration of 25 µM (FIG. 1a). The inactivation of VSV added to a red blood cell concentrate (RBC concentration= $1 \times 10^{10}$/ml; FIG. 1b) was similar to that observed in whole blood (FIG. 1a). Complete inactivation of VSV added to whole blood first diluted 5-fold (FIG. 1c) or to a red blood cell concentrate first diluted 2-fold (FIG. 1d) with PBS occurred at a lower AlPc concentration for a given light fluence than that observed with their undiluted counterparts. VSV inactivation did not occur in the absence of AlPc or in the dark (data not shown).

Red blood cell integrity, as determined by hemoglobin released during the treatment period, was well maintained (lysis >2%) under each of the conditions presented in FIG. 1.

Cell-free EMC, a non-enveloped virus, was not inactivated on treatment with AlPc when evaluated under conditions similar to those described above (data not shown).

Example 2

Intracellular VSV was prepared as described hereinabove. Comparison of the concentration of cells harvested following trypsin treatment ($2.07 \times 10^7$/ml) to viral infectious units ($1 \times 10^6$ TCID$_{50}$/50 µl; $2.0 \times 10^6$ TCID$_{50}$/ml) suggests that virtually every cell contained infectious virus. This intracellular VSV, added to a red blood cell concentrate, was completely inactivated ($\geq 10^{5.6}$ TCID$_{50}$) on treatment of this red cell concentrate with 10 μM AlPc and 88 J/cm$^2$ (Table I). Comparison with the results reported with cell-free virus (FIG. 1b) indicates that inactivation of the cell-associated form is more difficult. Red blood cell structure and function were unaffected.

TABLE I

Inactivation of Intracellular VSV Added to a Red Cell Concentrate with AlPc

| AlPc Concentration (μM) | VSV Titer(log$_{10}$) | | |
|---|---|---|---|
| | Dark | Light* | Log$_{10}$ Kill |
| 0 | 5.2 | 5.1 | 0.0 |
| 0 | 5.0 | 3.6 | 1.5 |
| 2 | 5.1 | ≦−0.5 | ≧5.6 |
| 5 | 5.3 | ≦−0.5 | ≧5.6 |
| 10 | | | |
| Av | 5.1 | | |

*88 J/cm$^2$

Example 3

Figure 2A:
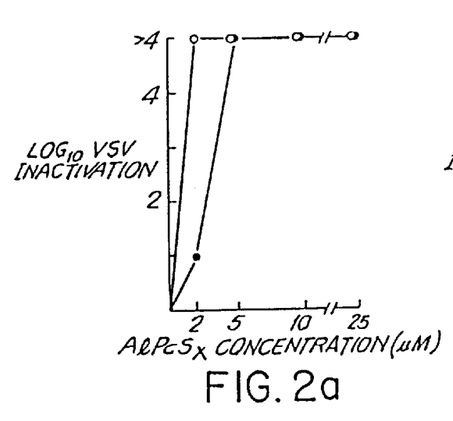
FIG. 2a depicts the results using $AlPcS_2$ with whole blood.
Figure 2B:
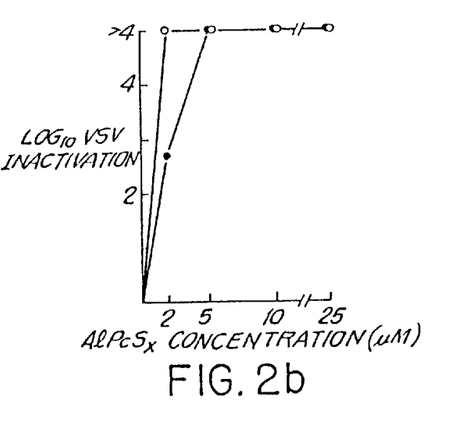
FIG. 2b depicts the results using $AlPcS_2$ with a red blood cell concentrate.
Figure 2C:
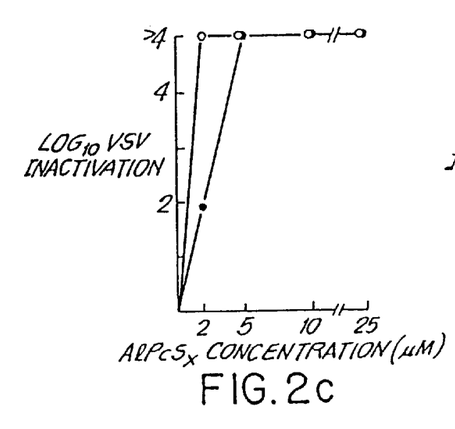
FIG. 2c depicts the results using $AlPcS_4$ with whole blood.
Figure 2D:
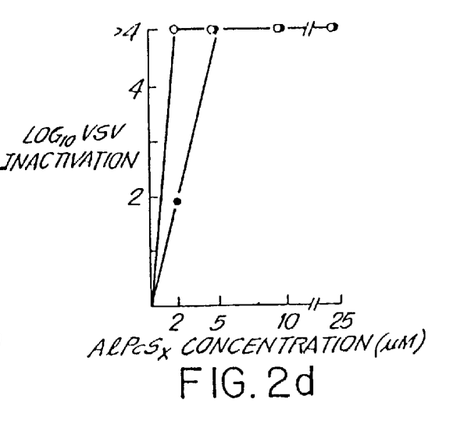
FIG. 2d depicts the results using $AlPcS_4$ with a red blood cell concentrate.

The inactivation of cell-free VSV in the presence of the di- and tetra-sulfonated derivatives of AlPc was also examined. Cell-free VSV and AlPcS$_2$ (FIG. 2a and FIG. 2b) or AlPcS$_4$ (FIG. 2c and FIG. 2d) at the indicated concentration were added to whole blood (FIG. 2a and FIG. 2c) or a red blood cell concentrate (FIG. 2b and FIG. 2d). Other details are as described above with respect to FIG. 1. Complete inactivation (≧10$^4$ TCID$_{50}$) of VSV with the sulfonated derivatives occurred at a lower AlPc concentration for a given light fluence than that observed with the non-sulfonated form (FIG. 1 vs. FIG. 2). Complete inactivation of VSV added to either whole blood diluted 5-fold or a red cell concentrate diluted 2-fold with PBS was observed with 2 μM of either sulfonated derivative and a light fluence of 44 J/cm$^2$ (data not shown). With regard to hemoglobin release during the course treatment, little (≦2%) was observed at AlPcS$_x$ concentrations up to 25 μM and a light fluence up to 176 J/cm$^2$ (Table II).

TABLE II

Percent Hemoglobin Released on Treatment of A Red Cell Concentrate with AlPc Derivatives

| AlPc Derivative | Light Fluence (J/cm$^2$) | Percent Hemoglobin Released AlPc conc: | | |
|---|---|---|---|---|
| | | 5 μm | 10 μM | 25 μM |
| AlPc | 88 | 1.1 | 0.8 | 1.1 |
| | 176 | 1.5 | 0.9 | 1.4 |
| AlPcS$_2$ | 88 | 0.6 | 0.5 | 0.3 |
| | 176 | 0.6 | 0.5 | 0.4 |
| AlPcS$_4$ | 88 | 0.2 | 0.5 | 0.3 |
| | 176 | 0.3 | 0.5 | 0.3 |

Example 4
Inactivation of HIV By AlPc

HIV in either a cell-free or intracellular form was added to either whole blood or a red cell concentrate in a test tube. Treatment of cell-free HIV used 1.0 μM AlPc and 176 J/cm$^2$; treatment of intracellular HIV used 5 μM AlPc and 44 J/cm$^2$. At the conclusion of treatment, the samples were processed as described above and HIV antigen measurements were made.

Treatment of whole blood or a red cell concentrate with AlPc was shown to inactivate ≧10$^{4.2}$TCID50 of cell-free and ≧10$^{3.6}$TCID$_{50}$ of a intracellular HIV (Table III). Red blood cell structure and functions were unaffected.

TABLE III

INACTIVATION OF HIV

| | Log$_{10}$ Inactivation | |
|---|---|---|
| | Cell-Free | Intracellular |
| Whole Blood | ≧4.2 | ≧3.6 |
| Red Cell Concentrate | ≧4.2 | not done |

Example 5
Red Blood Cell Integrity

Typical results of the percent hemoglobin released from red blood cells during the course of treatment with AlPc derivatives are given in Table II. The percent released varied between 0.2 and 1.5% of the total hemoglobin present.

Figure 3:
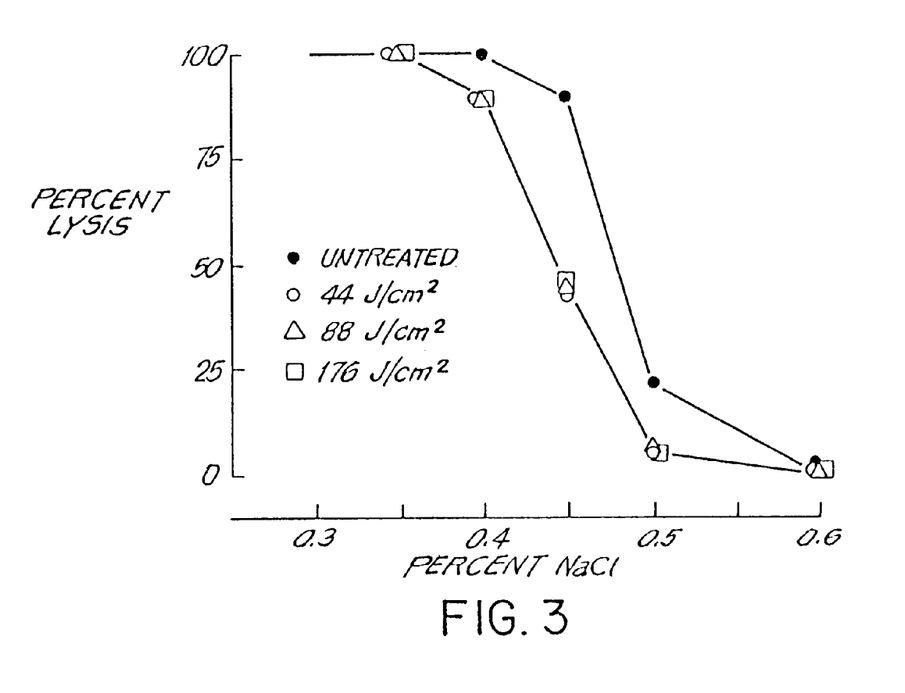
FIG. 3 is a graph depicting erythrocyte osmotic fragility prior to and following treatment with AlPc.

The erythrocyte osmotic fragility following treatment of whole blood was measured with no prior removal of AlPc (FIG. 3). Whole blood was treated with 10 μM AlPcCl and a light fluence of 44 J/cm$^2$ (open circles), 88 J/cm$^2$ (open triangles) and 176 J/cm$^2$ (open squares). Following treatment and with no subsequent processing, the erythrocyte osmotic fragility was determined in these samples and in the untreated control (closed circles) by dilution into solutions of saline at the indicated concentration. Following incubation for 30 minutes and centrifugation, released hemoglobin was measured with Drabkin's solution and compared with that released on dilution into distilled water.

As compared with the untreated control, treatment with 10 μM AlPc at light fluences of 44, 88 and 176 J/cm$^2$ increased the resistance of the red cells to osmotic shock.

Example 6

To evaluate the storage stability of treated red cells, 3 ml of whole blood were treated with 10 μM AlPc and a light fluence of 176 J/cm$^2$, as in Example 1. Following a storage period of 17 days, released hemoglobin was 1.8% of the total and the pH of the sample was 6.9, indicative of excellent storage compatibility.

Example 7

A study of VSV inactivation in an intact red cell concentrate unit was conducted. A red cell concentrate contained in a Fenwal 5J359 blood bag was illuminated from one side only. The inactivation of all detectable cell-free VSV (≧10$^{4.5}$ TCID$_{50}$) was achieved with 10.5 μM AlPc and a light fluence of 264 J/cm$^2$ corresponding to a treatment duration of 3 hours (Table IV). A 10-fold more sensitive macroculture assay did not show the presence of VSV (kill ≧10$^{5.5}$ TCID$_{50}$) at 352 and 396 J/cm$^2$. Less than 2% lysis was observed even at 396 J/cm$^2$.

TABLE IV

Inactivation of Cell-Free VSV Added to An Individual Red Cell Concentrate Unit

| AlPc Concentration (μM) | Light Fluence (J/cm$^2$) | VSV Titer (log$_{10}$ TCID$_{50}$) |
|---|---|---|
| 0 | 0 | 4.0 |
| 10.5 | 88 | 2.8 |
| 10.5 | 176 | 1.3 |

TABLE IV-continued

Inactivation of Cell-Free VSV Added to An
Individual Red Cell Concentrate Unit

| AlPc Concentration ($\mu$M) | Light Fluence (J/cm$^2$) | VSV Titer (log$_{10}$ TCID$_{50}$) |
|---|---|---|
| 10.5 | 264 | $\leq$-0.5 |
| 10.5 | 352 | $\leq$-0.5 |
| 10.5 | 396 | $\leq$-0.5 |

Example 8

An assessment of the effect of phthalocyanine treatment on platelet function was conducted. Zinc phthalocyanine (ZnPc) in dimethylformamide was added to a platelet concentrate containing 5.36×10$^9$ platelets/mL and a plasma protein concentration of 60 mg/mL. The final concentration of ZnPc was 20 $\mu$M. At the indicated times, platelet count was determined, platelet morphology was assessed by measurement of mean volumes, and the ability of platelets to aggregate on addition of adenosine diphosphate (ADP) was assessed (Table V). Through the total treatment time, platelet count was maintained to the extent of 86–91%. The mean volume of the platelets was unaffected. Aggregation in response to ADP, expressed either in terms of the initial rate of aggregation or the extent of aggregation was unchanged as compared with the DMF only control for 10 minute light exposure, though somewhat decreased for 15 and 30 minute light exposures.

TABLE V

Effect of Zinc Phthalocyanine on Platelets

| Sample | Platelet Count (×10$^{-9}$/mL) | Mean Platelet Volume (micron$^3$) | Aggregation Response Initial Rate (A/min) | Aggregation Response Maximum Extent (A) |
|---|---|---|---|---|
| Controls | | | | |
| No light, no ZnPc | 5.36 | 6.1 | 38 | 45 |
| Solvent (DMF) only | 5.65 | 6.4 | 34 | 26 |
| Test | | | | |
| ZnPC + 10 minute light | 4.74 | 6.3 | 35 | 28 |
| ZnPC + 15 minute light | 4.87 | 6.1 | 25 | 22 |
| ZnPC + 30 minute light | 4.63 | 5.8 | 25 | 20 |

Example 9

The Effect of Red Cell Concentration on AlPcS$_4$-Induced Lysis

Human red blood cells were washed twice with phosphate buffered saline to remove plasma and then diluted to the indicated concentration. Aluminum phthalocyanine tetrasulfonate (10 $\mu$M) was added to each and the samples irradiated as described above with 88 J/cm$^2$. Following irradiation, the degree of lysis was determined by the amount of hemoglobin released. As shown in Table VI, 100% lysis was observed with a red cell concentration of 4.5×10$^8$ cells/ml, but improved suddenly when the cell concentration was raised to 2.25×10$^9$ cells/ml or higher.

TABLE VI

Percent Hemolysis As a Function of Red Cell Concentration

| Red Cell Conc (cells/ml) | Percent Hemolysis |
|---|---|
| 9 × 10$^9$ | 2.9 |
| 4.5 × 10$^9$ | 2.9 |
| 2.25 × 10$^9$ | 2.7 |
| 4.5 × 10$^8$ | 100 |

Example 10

Comparison Of Virus Kill Of Aluminum Phthalocyanine With Hematoporphyrin Derivative Vesicular stomatitis virus (VSV) was added to whole blood followed by either hematoporphyrin derivative (HPD), a dye with an absorption maximum below 630 nm, or aluminum phthalocyanine sulfonate. Each was exposed to light as above. The results (Table VII below) indicate that virus kill is both faster and more complete with AlPcS$_4$ than with HPD.

TABLE VII

| Compound | Conc ($\mu$M) | VSV Kill (log$_{10}$) 30 min | VSV Kill (log$_{10}$) 120 min |
|---|---|---|---|
| HPD* | 18 | 1.3 | 1.4 |
| | 36 | 1.4 | 2.4 |
| | 54 | 1.7 | 4.0 |
| AlPcS$_4$ | 5 | $\geq$4.0 | $\geq$4.0 |

*Assumed MW of 1106

Example 11

Circulatory half-life of autologous, rabbit red blood cells treated with aluminum phthalocyanine derivatives in the presence of quenching agents.

A rabbit red blood cell concentrate (RBCC) containing 1×10$^{10}$ RBC/ml suspended in plasma was mixed with aluminum phthalocyanine tetrasulfonate (AlPcS$_4$) and, where indicated, a quenching agent added. The mixture was then exposed to 25 mW/cm$^2$ of visible light for 30 minutes, after which the treated RBCC was washed by centrifugation, labeled with $^{51}$Cr, and administered intravenously into the rabbit of origin. The results indicate that RBC treated in the presence of the added quenching agent had near normal circulatory in vivo survival whereas the RBC treated without the added quenching agent had a shortened in vivo circulatory survival (Table VIII).

The aluminum phthalocyanine derivative and quenching agent were added to a separate RBCC sample containing vesicular stomatitis virus and exposed to similar irradiation conditions. The inactivation of virus was unaffected by the addition of quencher (Table VIII).

TABLE VIII

In vivo circulatory survival of
rabbit red blood cells after treatment with AlPcS4

| Dye | Quencher | Half-life (days) | Log$_{10}$ VSV Kill |
|---|---|---|---|
| 10 $\mu$M AlPcS4 (Dark Control) | 4 mM glutathione | 12.5 | 0 |

TABLE VIII-continued

In vivo circulatory survival of rabbit red blood cells after treatment with AlPcS4

| Dye | Quencher | Half-life (days) | $\text{Log}_{10}$ VSV Kill |
|---|---|---|---|
| 10 μM AlPcS4 | NONE | 3.75 | ≧5.5 |
| 10 μM AlPcS4 | 1 mM mannitol | 6 | ≧5.5 |
| 10 μM AlPcS4 | 1 mM tryptophan | 8 | ≧5.5 |
| 10 μM AlPcS4 | 1 mM glutathione | 10.5 | ≧5.5 |

Example 12

Aggregation response of platelets treated with a psoralen derivative in the presence of absence of added quenching agent.

The virucidal and functional effects on platelet concentrates were assessed after the addition of 25 μg/ml of 4'-aminomethyl-4,5',8-trimethylpsoralen (AMT) with and without the presence of the quenching agent, reduced glutathione (GSH). The samples were irradiated with 6.5 mW/cm$^2$ of UVA light for 20–30 min. in the presence of oxygen. Platelet aggregation extent and rate in response to collagen, measured 24 hours after treatment, improved in the presence of GSH (Table IX). This was especially evident with 30 min. UVA exposure, conditions needed to achieve complete virus kill.

TABLE IX

The effect of the addition of GSH on the extent/rate of aggregation in platelets after UVA treatment with AMT.

| AMT μg/ml | GSH | Exposure Time | Platelet Extent | Aggregation (% control) Rate | $\text{Log}_{10}$ VSV Kill |
|---|---|---|---|---|---|
| 25 | 0 | 20 min | 98 | 75 | 4.1 |
| 25 | 1 mM | 20 min | 100 | 84 | 4.5 |
| 25 | 0 | 30 min | 88 | 63 | ≧5.5 |
| 25 | 1 mM | 30 min | 98 | 90 | ≧5.1 |

Example 13

Improved process recovery of coagulation factors on treatment of plasma with AMT and UVA with addition of quenchers.

Human plasma was treated with 25 μg/ml of AMT and exposed to 6.5 mW/cm$^2$ of UVA light for 20 minutes. Virus kill measurement and process recovery of coagulation factors were compared after treatment with and without the addition of glutathione. In the absence of reduced glutathione (GSH), or in the presence of 1 mM and 4 mM GSH, the extent of virus kill was 5.1, 5.3 and 5.3 $\log_{10}$, respectively. While AHF recovery in the absence of GSH was only 77%, recovery increased to essentially 100% in the presence of 4 mM GSH.

TABLE X

Process recovery of coagulation factor VIII following treatment of human plasma with AMT and quenching agent.

| | GSH Concentration | | |
|---|---|---|---|
| | NONE | 1 mM | 4 mM |
| Virus Kill (TCID$_{50}$) Factor VIII Recovery | 5.1 | 5.3 | 5.3 |
| Untreated (u/ml) | 1.24 | — | — |
| Treated (u/ml) | 0.95 | 1.16 | 1.26 |
| % Recovery | 77% | 94% | 102% |

Example 14

The enhancement in the recovery of plasma coagulation factors treated to inactivate viruses with AMT; reduction of oxygen content versus use of quenchers.

Human plasma was treated with 25 μg/ml AMT under normal atmospheric conditions in the presence and absence of 1 mM glutathione added as a quencher, versus treatment under reduced oxygen concentration through exchange with nitrogen gas. Normally aerated samples were irradiated with UVA light for 20 minutes while deoxygenated samples had to be irradiated for 120 minutes to provide approximately the same virus kill. The data indicate that, as compared to treatment of normally aerated plasma in the absence of quencher, (1) the addition of 1 mM glutathione enhances AHF recovery without compromising virus kill, (2) a high level of virus kill and a high recovery of coagulation factor recovery can be achieved by reducing oxygen content, provided the treatment period is extended, and (3) the use of quencher obviates the need to perform a gas exchange and reduces the duration of treatment required for a high level of virus kill.

TABLE XI

The recovery of coagulation factor VIII in plasma on treatment with AMT; effect of quencher addition versus deoxygenation.

| Treatment Conditions | AMT (μg/ml) | UVA Duration (min) | VSV Kill ($\log_{10}$) | AHF Recovery (%) |
|---|---|---|---|---|
| Normally aerated | 25 | 20 | 5.1 | 77 |
| Normally aerated + 1 mM GSH | 25 | 20 | 5.3 | 94 |
| Deaerated | 25 | 120 | ≧6.1 | 91 |

Example 15

Improved Virus Kill in Platelets Treated with a Psoralen Derivative: Effect of Quencher Addition Versus Deoxygenation A standard blood bank platelet concentrate was treated with 25 μg/ml of AMT and exposure to UVA (6.5 mW/CM$^2$). Prior to treatment, where indicated, oxygen in the normally aerated platelets was exchanged for nitrogen by displacing the gas above the solution using nitrogen, equilibrating for 1 minute, and repeating the process three times. Alternately, 1 mM of the quencher glutathione was added prior to treatment. The rate of inactivation of vesicular stomatitis virus, added to the sample and serving as a viral marker, was assessed throughout the duration of UVA exposure. The aggregation response of the platelets was assessed 24 hours following treatment in the presence of collagen. The results indicate that virus kill occurred more quickly in the normally aerated sample containing quencher than in the deaerated sample (Table XII). Excellent platelet functional recovery was achieved in each case when measured at 24 hours. Thus the use of quencher avoids the tedious and potentially time consuming step of gas exchange without sacrifice of virus kill or platelet functionality.

TABLE XII

| Duration of UVA (Minutes) | VSV Titer ($log_{10}$) | |
| --- | --- | --- |
| | $O_2$ + 1 mM Glutathione | Deaerated |
| Start | 5.0 | 5.0 |
| 10 | 3.1 | — |
| 20 | 1.4 | — |
| 30 | $\leq$ −0.5 | — |
| 60 | $\leq$ −0.5 | 2.4 |
| 90 | $\leq$ −0.5 | 1.4 |
| 120 | $\leq$ −0.5 | $\leq$ −0.5 |

It will be appreciated that the instant specification is set forth by way of illustration and not limitation, and that various modifications and changes may be made without departing from the spirit and scope of the present invention.

What is claimed is:

1. A process for inactivating an extracellular lipid enveloped human pathogenic virus and/or an intracellular human pathogenic virus which may be present in a blood cell composition, comprising contacting said composition with a virucidally effective amount of a photoreactive compound having an absorption maximum of $\geq$630 nm, light and a quencher, wherein said composition contains $\geq$2.25×10$^9$ cells/ml.

2. A process for inactivating an extracellular lipid enveloped human pathogenic virus and/or a intracellular human pathogenic virus which may be present in a blood cell composition containing $\geq$2.25×10$^9$ cells/ml while retaining structural integrity of greater than 80% of one type of blood cell contained within said composition, comprising contacting said composition with a virucidally effective amount of at least one photoreactive compound having an absorption maximum of $\geq$630 nm, light and a quencher.

3. The process according to claim 2, wherein the blood cell composition comprises at least one component selected from the group consisting of red blood cells, platelets and whole blood.

4. The process according to claim 3, wherein the red blood cells and/or platelets are concentrated.

5. The process according to claim 2, wherein the type of blood cell is red blood cells and the structural integrity of said red blood cells is ascertained by assessing the amount of hemoglobin released after treatment of said composition with said photoreactive compound, light and a quencher, a release of less than 20% of hemoglobin indicates that the structural integrity of greater than 80% of said red blood cells was retained after treatment with said photoreactive compound, light and a quencher.

6. The process according to claim 2, wherein the type of blood cell is platelets and the structural integrity of said platelets is ascertained by counting the number of platelets remaining after treatment of said composition with said photoreactive compound, light and a quencher, a retention of greater than 80% of said platelets indicates that the structural integrity of greater than 80% of said platelets was retained after treatment with said photoreactive compound, light and a quencher.

7. The process according to claim 2, wherein oxygen is present during the process.

8. The process according to claim 2, wherein the light is visible light at a wave length of 630 nm–700 nm.

9. The process according to claim 2, wherein the photoreactive compound is phthalocyanine.

10. The process according to claim 2, wherein the extracellular lipid enveloped human pathogenic virus and/or the intracellular human pathogenic virus is a human immunodeficiency virus (HIV).

11. A process for preparing a blood cell composition suitable for transfusion into a recipient in need of such transfusion which comprises inactivating an extracellular lipid enveloped human pathogenic virus and/or an intracellular human pathogenic virus which may be present in said composition according to the process of claim 2.

12. A process for inactivating a human immunodeficiency virus (HIV) which may be present in a blood cell composition containing $\geq$2.25×10$^9$ cells/ml while retaining structural integrity of greater than 80% of one type of blood cell contained within said composition, comprising contacting said composition with a virucidally effective amount of a photoreactive compound having an absorption maximum of $\geq$630 nm, light and a quencher.

13. A process for inactivating an extracellular lipid enveloped human pathogenic virus and/or an intracellular human pathogenic virus which may be present in a composition containing a coagulation factor while retaining $\geq$94% of said coagulation factor, consisting essentially of contacting said composition which a virucidally effective amount of a photoreactive compound, light and a quencher.

14. The process according to claim 13, wherein the photoreactive compound is a psoralen and the light is UVA.

15. The process according to claim 13, wherein the quencher is glutathione.

16. The process according to claim 13, wherein the photoreactive compound is phthalocyanine and the light is visible light at a wavelength of 630 nm to 700 nm.

17. The process according to claim 13, wherein said composition is human plasma.

18. The process according to claim 13, wherein the coagulation factor is Factor VIII.

19. The process according to claim 13, wherein the extracellular lipid enveloped human pathogenic virus and/or the intracellular human pathogenic virus is a human immunodeficiency virus (HIV).

20. A process for preparing a blood cell composition suitable for transfusion into a recipient in need of such transfusion which comprises inactivating an extracellular lipid enveloped human pathogenic virus and/or an intracellular human pathogenic virus which may be present in said composition according to the process of claim 13.

21. A process for inactivating a human immunodeficiency virus (HIV) which may be present in a composition containing at least one coagulation factor while retaining $\geq$94% of said coagulation factor, comprising contacting said composition with a virucidally effective amount of at least one photoreactive compound having an absorption maximum of $\geq$630 nm, light and a quencher.

* * * * *